United States Patent
Berman et al.

(10) Patent No.: US 6,917,430 B2
(45) Date of Patent: Jul. 12, 2005

(54) METHOD TO IMPROVE THE CONTROL OF SOURCE CHEMICALS DELIVERY BY A CARRIER GAS

(75) Inventors: Michael Berman, Portland, OR (US); Scott Gould, Boring, OR (US)

(73) Assignee: LSI Logic Corporation, Milpitas, CA (US)

( * ) Notice: Subject to any disclaimer, the term of this patent is extended or adjusted under 35 U.S.C. 154(b) by 342 days.

(21) Appl. No.: 10/172,849

(22) Filed: Jun. 17, 2002

(65) Prior Publication Data

US 2003/0231313 A1 Dec. 18, 2003

(51) Int. Cl.[7] .............................................. G01N 21/00

(52) U.S. Cl. .................... 356/432; 356/436; 356/437

(58) Field of Search ................................. 356/432–437; 250/343

(56) References Cited

U.S. PATENT DOCUMENTS 4,692,621 A * 9/1987 Passaro et al. .............. 250/343

* cited by examiner

Primary Examiner—Gregory J. Toatley, Jr.
Assistant Examiner—Amanda Merlino
(74) Attorney, Agent, or Firm—Trexler, Bushnell, Giangiorgi & Blackstone, Ltd.

(57) ABSTRACT

A method and control system for controlling the delivery of a source chemical by a carrier gas. The carrier gas is delivered to a vessel containing the source chemical, and a flow of source chemical and carrier gas is carried from the vessel along a flow line. A sensor is used to detect light absorption of the flow, and the flow is adjusted based on what is detected. The sensor provides that light is directed transversely through the flow line and that the intensity of the light which passes through the flow line is detected by a detector. The detector forwards an output signal to a signal processing unit which thereafter adjusts the flow based on what was detected. The light may be filtered. The flow line includes at least a portion which provides an optical window for allowing light to pass therethrough.

17 Claims, 2 Drawing Sheets

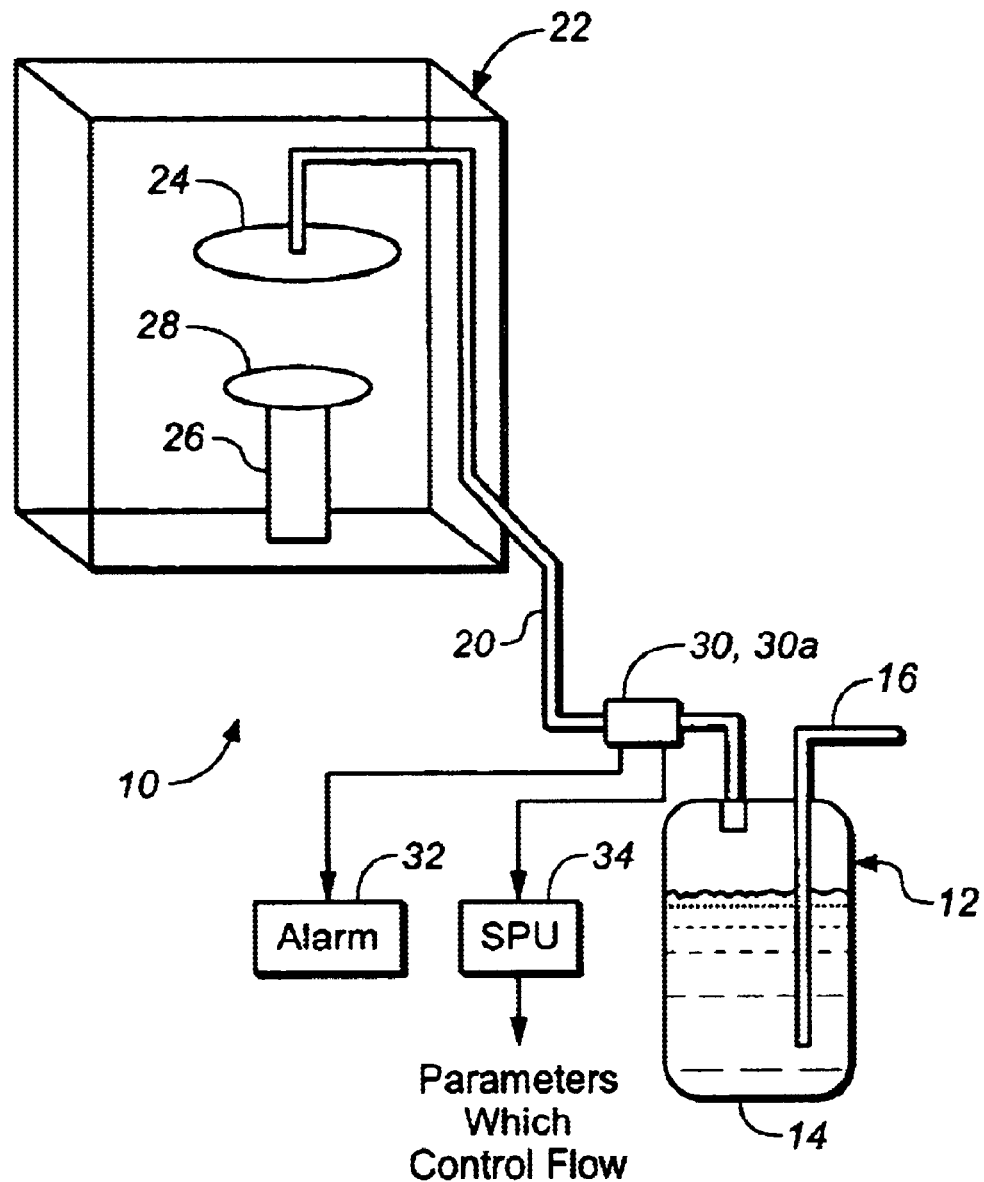
FIG._1

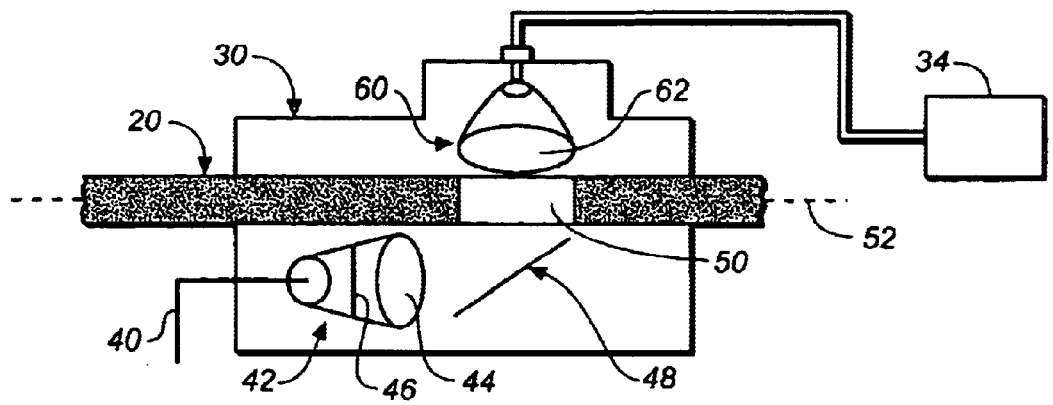
FIG._2
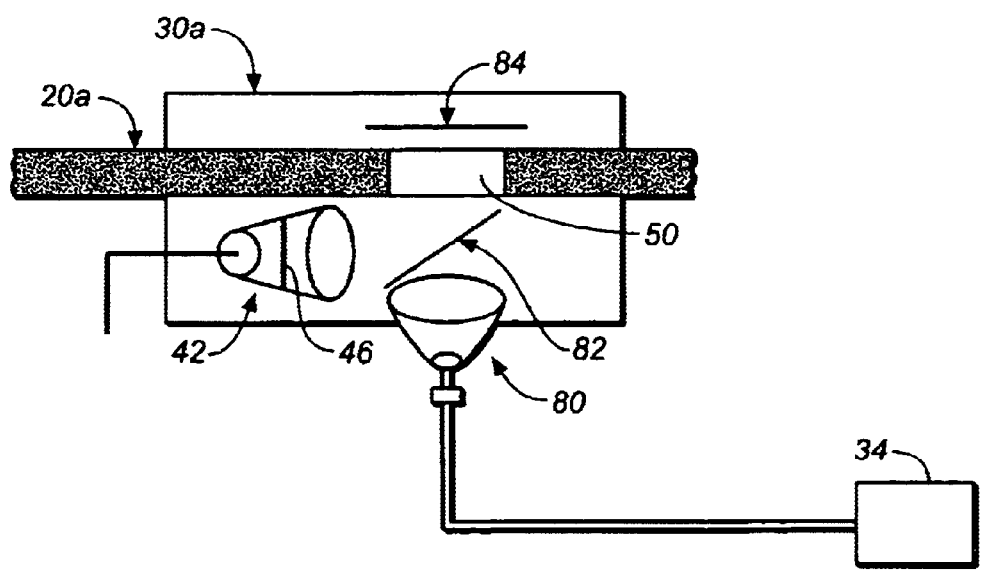
FIG._3

METHOD TO IMPROVE THE CONTROL OF SOURCE CHEMICALS DELIVERY BY A CARRIER GAS

BACKGROUND

The present invention generally relates to methods and apparatuses for controlling source chemical delivery by a carrier gas, and more specifically relates to a method and apparatus for controlling source chemical delivery by a carrier gas where the delivery is controlled based on detected light absorption properties of the flow.

Chemical applications exits where a source chemical is delivered using a carrier gas. Specifically, the carrier gas is bubbled up through the source chemical (a liquid) contained in a vessel, and is delivered to, for example, a processing chamber. When the carrier gas "bubbles" through the source chemical to the top of the vessel, molecules of the source chemical attach to the carrier gas and is carried to the processing chamber. One such application is the processing of wafers (i.e., in the manufacture of semiconductor devices). In such an application, a typical source chemical may include TEOS (tetraethylorthosilicate), TMB (trimethylborate), TEPO (triethyiphosphate), TMP (trimethylphosphite), TMPO (triethyiphosphate) or POCL (phosphorusoxychloride) (and many others), and a typical carrier gas may include He (Helium) or $N_2$ (Nitrogen).

The amount of source chemical carried into the processing chamber is not typically constant, and changes based on several different factors or parameters, such as the amount of source chemical contained in the vessel, the concentration of dopant in the source chemical, the temperature of the vessel, the temperature of the carrier gas, pressure of the carrier gas, flow of the carrier gas, etc. As the amount of source chemical attached to the carrier gas changes, the process in the processing chamber also changes.

Presently, the delivery of source chemical using a carrier gas is controlled based on indirect measurements of the many factors or parameters which affect the delivery. However, inputs can and do change, and the amount of source chemical delivered using the carrier gas changes despite the desire to have such delivery be constant and be directly and predictably controlled. In the case of wafer processing, such undesirable variance in the amount of source chemical delivered results in undesired changes in the thicknesses of films being deposited on the wafer. This is evidenced in the outputs of the process, and is a direct result of the inconsistent and unreliable control of the reactants to the process In other words, direct measurement of the reactant (i.e., the concentration of source chemical being delivered by the carrier gas) is not performed and instead, the delivery of source chemical is controlled through monitoring those parameters which affect the delivery. Such a process provides a method of delivering source chemical which is relatively unpredictable and unreliable.

OBJECTS AND SUMMARY

A general object of an embodiment of the present invention is to provide a method and apparatus where the amount of source chemical being delivered by a carrier gas is directly monitored by detecting light absorption of the source chemical by use of spectroanalysis.

Another object of an embodiment of the present invention is to provide a method and apparatus wherein a light absorption property of a flow of source chemical and carrier gas is monitored to control delivery of source chemical.

Still another object of an embodiment of the present invention is to provide a method and apparatus wherein a sensor is used on a flow line to sense light absorption of the flow through the fluid line to control delivery of a source chemical.

Still yet another object of an embodiment of the present invention is to provide a method and apparatus which provides that the delivery of a source chemical using a carrier gas can be more directly and predictably controlled.

Briefly, and in accordance with at least one of the foregoing objects, an embodiment of the present invention provides a method and control system for controlling the delivery of a source chemical by a carrier gas. The carrier gas is delivered to a vessel containing the source chemical, and a flow of source chemical and carrier gas is carried from the vessel along a flow line. A sensor is used to detect the light absorption spectra of the flow, and thereafter the flow may be adjusted based on what is detected. The sensor provides that light is directed (and possibly filtered beforehand) transversely through the flow line and that the intensity of one or more wavelengths of the light which passes through the flow line is detected by a detector. The detector may output an alarm and/or may forward an output signal to a signal processing unit which thereafter adjusts the flow based on a closed loop feed back to maintain a constant amount of source chemical being supplied to the processing chamber. To facilitate the passage of light transversely through the flow line, the flow line preferably includes an optical window which may be made of glass, quartz or fused silica, for example.

BRIEF DESCRIPTION OF THE DRAWINGS

The organization and manner of the structure and operation of the invention, together with further objects and advantages thereof, may best be understood by reference to the following description, taken in connection with the accompanying drawings, wherein:

FIG. 1 illustrates a control system for controlling the delivery of a source chemical by a carrier gas, where the control system is in accordance with an embodiment of the present invention and provides that a light absorption property of flow of source chemical and carrier gas from a vessel to a processing chamber is monitored using a sensor on the flow line;

FIG. 2 illustrates one possible embodiment of the sensor included in the control system shown in FIG. 1; and FIG. 3 illustrates another possible embodiment of the sensor included in the control system shown in FIG. 1.

DESCRIPTION

While the invention may be susceptible to embodiment in different forms, there are shown in the drawings, and herein will be described in detail, specific embodiments with the understanding that the present disclosure is to be considered an exemplification of the principles of the invention, and is not intended to limit the invention to that as illustrated and described herein.

FIG. 1 depicts a control system which is in accordance with an embodiment of the present invention. The control system provides that a sensor is used to detect light absorption of flow of source chemical and carrier gas. Thereafter, the flow may be adjusted based on what is detected. As such, the delivery of source chemical, such as in a wafer processing application, can be directly and predictably controlled.

As shown in FIG. 1, the control system 10 includes a vessel 12 which contains a source chemical (i.e., liquid) 14.

Such source chemical may take many forms. A gas line 16 delivers carrier gas to the vessel 12, and the carrier gas may also take many forms. For example, as discussed above, in a wafer processing application, the source chemical 14 may be TEOS, TMB, TEPO, TMP, TMPO, POCL, or some other source chemical, and the carrier gas may be any inert or carrier gas, for example, Helium or Nitrogen. Regardless of the actual materials used, the control system 10 is configured such that the carrier gas bubbles up through the source chemical 14, and as a result, molecules of the source chemical attach to the carrier gas.

A flow line 20 carries a flow of source chemical and carrier gas (i.e., source chemical attached to the carrier gas) from the vessel 12 to a processing chamber 22. As shown in FIG. 1, the processing chamber 22 may be a wafer processing chamber wherein a showerhead 24 (which is one of many ways of dispensing source chemical within such a process) is disposed over a wafer chuck and pedestal 26 on which a wafer 28 sits during processing. The showerhead 24 is attached to the flow line 20. Hence, during processing, source chemical 14 flows out of the showerhead 24 onto the wafer 28.

As shown in FIG. 1, the control system 10 provides that a sensor 30, 30a is disposed along the flow line 20 from the vessel 12 to the processing chamber 22. The sensor 30, 30a is configured to provide that a light absorption property of the flow of source chemical and carrier gas (i.e., source chemical attached to the carrier gas) along the flow line 20 can be monitored. The sensor 30, 30a may be configured to emit an alarm signal using an alarm 32 and/or may provide an output signal to a signal processing unit 34, where the output signal indicates the light absorption property of the flow of source chemical and carrier gas which was detected by the sensor 30, 30a. The signal processing unit 34 thereafter controls/adjusts one or more parameters of the control system 10 which affects the delivery of source chemical 14 along the flow line 20 to the processing chamber 22. As such, the delivery of source chemical 14 to the processing chamber 22 is controlled based upon what is detected regarding the ability of the flow between the vessel 12 and processing chamber 22 to absorb light.

FIGS. 2 and 3 depict two different exemplary structures of the sensor 30, 30a which may be used in connection with the control system shown in FIG. 1. Specifically, FIG. 2 depicts sensor 30 while FIG. 3 depicts sensor 30a. The sensor 30 shown in FIG. 2 provides that a power input 40 supplies power to a light source or light collimator 42, where the light source 42 may be, for example, infrared, in the visible spectrum, or ultraviolet. The light source 42 includes an output lens 44 for outputting light generated by the light source 42. The light source 42 may be configured such that the light is broadband or a single wavelength. Preferably, the light covers the spectrum of a primary absorption peak of the source chemical. As shown in FIG. 2, if the light is broadband, preferably a band pass filter 46 is used.

The light source 42 is positioned such that the light is directed at a mirror 48 which re-directs the light at the flow line 20 which delivers the flow of source chemical and carrier gas from the vessel 12 to the processing chamber 22 (see FIG. 1). As shown in FIG. 2, at least a portion of the flow line 20 provides an optical window 50 which allows the light from the mirror 48 to pass transversely through the flow line (i.e., generally perpendicular to a longitudinal axis 52 of the flow line 20). The optical window 50 may be formed of, for example, glass, quartz, fused silica or any other material which would allow the light to pass transversely through the flow line 20 and is transparent to the wavelength of the peaks being monitored.

Positioned on the other side of the flow line 20 from the mirror 48 is a detector 60 which is configured to detect the light which shines through the optical window 50 of the flow line 20. As such, the detector 60 includes an input collimator 62. Specifically, the detector 60 is configured to detect the amplitude of the light which passes transversely through the flow line 20. As such, the detector 60 effectively detects a light absorption property of the flow in the flow line 20. Each of the source chemicals which would be used has a light absorption characteristic at one or more set wavelengths. The absorption may be in the infrared, visible or ultraviolet wavelengths. For each source chemical, there is one or more wavelengths which have a measurable absorption peak. Preferably, the light source 42 is configured such that the light which is passed transversely through the flow line 20 (i.e., through the optical window 50) has a strong output at the wavelength of the main absorption peak, a wavelength which provides that there is little interference provided by the carrier gas in the flow along the flow line. Preferably, the change in the intensity of the light is calibrated to provide a value for the amount of source chemical that is carried by the carrier gas in the flow line 20.

A change in light level detected by the detector 60 may work to effectively alarm that a high or low amount of source chemical is being carried by the carrier gas through the flow line 20. The detector may provide an alarm or, as shown in FIG. 1, may provide a signal to an alarm device 32. The change in light level detected may be used to control parameters which affect the delivery of source chemical to the processing chamber 22, such as inputs applied to the carrier gas or to the source chemical 14 or source chemical vessel 12, in order to maintain a constant amount of source chemical being delivered to the processing chamber 22. To this end, as shown in FIG. 2, the detector 60 may produce an output signal which is communicated to signal processing unit 34 (see also FIG. 1) which thereafter controls parameters which affect the delivery of the source chemical to the processing chamber. In other words, a closed loop feed back control system can be implemented to provide controlled delivery of source chemical based on what is detected about the light absorption of the flow through the flow line 20 between the vessel 12 and the processing chamber 22. As such, the absorption spectra of the source chemical in the carrier gas is used to monitor or control the flow of the source chemical into the processing chamber 22. Such a closed loop control system provides much better control on the process, such as on a wafer process wherein better film uniformity can be achieved.

While a light source 42 of infrared, visible or ultraviolet can be used, and this has been discussed above, other forms of energy can be used, such as radio frequency, NMR, x-ray florescent spectroscopy (XPS) or FTIR. Calibration of the signal could include integrations of the intensity to the flow of the carrier with feed back for improved delivery control.

FIG. 3 depicts an alternative sensor 30a which may be used in connection with the control system shown in FIG. 1. As shown, the sensor 30a is similar to that shown in FIG. 2 and includes a light source 42, possibly a filter, and a detector 80 which may be connected to an alarm component 32 (see FIG. 1) and/or signal processing unit 34. The difference between the sensor 30a shown in FIG. 3 and the sensor 30 shown in FIG. 2 is that the sensor 30a shown in FIG. 3 includes a beam splitter mirror 82 which is angled toward the flow line 20 and a 100% reflection mirror 84 on the opposite side of the flow line 20. The light source 42 directs light at the beam splitting mirror 82 and the beam splitting mirror 82 re-directs the light transversely through the optical window 50 in the flow line 20 toward the second mirror 84. The second mirror 84 reflects the light transversely through the flow line 20, toward and through the beam splitting mirror 82, to the detector 80.

While embodiments of the present invention are shown and described, it is envisioned that those skilled in the art may devise various modifications of the present invention without departing from the spirit and scope of the appended claims.

What is claimed is:

1. A method of controlling the delivery of a source chemical by a carrier gas, said method comprising: delivering the carrier gas to a vessel containing the source chemical in the form of a liquid, wherein the carrier gas is delivered in the liquid, below a liquid level of the liquid, wherein the carrier gas rises through the liquid carrying source chemical above the liquid level; carrying a flow of source chemical and carrier gas from above the liquid level in the vessel; detecting a light absorption property of the flow; and adjusting the flow based on the light absorption property of the flow which is detected.

2. A method as recited in claim 1, wherein the step of detecting a light absorption property of the flow comprises using a sensor.

3. A method as recited in claim 1, wherein the step of carrying a flow of source chemical and carrier gas from the vessel comprises carrying the flow from the vessel along a flow line, and the step of detecting a light absorption property of the flow comprises directing light transversely through the flow line and detecting an intensity of light which passes through the flow line.

4. A method as recited in claim 3, wherein the step of directing light transversely through the flow line comprises directing light at a mirror and using the mirror to re-direct the light transversely through the flow line toward a detector configured to detect an intensity of light which passes through the flow line.

5. A method as recited in claim 3, wherein the step of directing light transversely through the flow line comprises directing light at a beam splitting mirror and using the beam splitting mirror to re-direct the light transversely through the flow line toward a mirror, and using the mirror to reflect the light transversely through the flow line toward and through the beam splitting mirror to a detector configured to detect an intensity of the light.

6. A method as recited in claim 4, further comprising having the detector detect an intensity of light which passes through the flow line and forwarding an output signal from the detector to a signal processing unit.

7. A method as recited in claim 6, further comprising using the signal processing unit to adjust the flow based on the output signal received from the detector.

8. A method as recited in claim 3, further comprising filtering the light before directing the light transversely through the flow line.

9. A method as recited in claim 3, further comprising providing that the flow line includes at least a portion which provides an optical window for allowing light to pass therethrough.

10. A method as recited in claim 9, wherein the step of providing that the flow line includes at least a portion which provides an optical window for allowing light to pass therethrough comprises providing that the optical window is formed of glass, quartz, fused silica or another material that is transparent to the wavelength of the peaks being monitored.

11. A control system for controlling the delivery of a source chemical by a carrier gas, said control system comprising: a vessel configured to contain the source chemical in the form of a liquid, wherein the liquid has a liquid level; a fluid line configured to deliver the carrier gas to the vessel below the liquid level, wherein the carrier gas rises through the liquid carrying source chemical above the liquid level; a flow line configured to carry a flow of source chemical and carrier gas from above the liquid level in the vessel; a sensor along the flow line configured to detect a light absorption property of the flow; a signal conditioning unit connected to the sensor and configured to receive an output signal therefrom and adjust the flow of source chemical and carrier gas from the vessel along the flow line.

12. A control system as recited in claim 11, said sensor comprising a light source and a detector, wherein said sensor is configured to direct light transversely through the flow line and detect an intensity of light which passes through the flow line.

13. A control system as recited in claim 12, wherein the sensor further comprises a mirror, wherein said light source is configured to direct light at the mirror and the mirror is configured to re-direct the light transversely through the flow line toward the detector.

14. A control system as recited in claim 12, wherein the sensor further comprises a mirror and a beam splitting mirror, wherein said light source is configured to direct light at the beam splitting mirror, said beam splitting mirror configured to direct the light transversely through the flow line toward the mirror, said mirror configured to reflect the light transversely through the flow line toward and through the beam splitting mirror to the detector.

15. A control system as recited in claim 12, wherein the sensor further comprises a filter configured to filter the light before the light is directed transversely through the flow line.

16. A control system as recited in claim 11, wherein the flow line includes at least a portion which provides an optical window for allowing light to pass therethrough.

17. A control system as recited in claim 12, wherein the optical window is formed of glass, quartz, fused silica or another material that is transparent to the wavelength of the peaks being monitored.

* * * * *